(12) United States Patent
Fisher et al.

(10) Patent No.: US 11,229,424 B2
(45) Date of Patent: Jan. 25, 2022

(54) ROTATABLE SYRINGE SYSTEM

(71) Applicant: Praxis Holding LLC, Tampa, FL (US)

(72) Inventors: John Steele Fisher, Belleair, FL (US); Wayne A. Noda, Mission Viejo, CA (US)

(73) Assignee: Praxis Holding LLC, Tampa, FL (US)

( * ) Notice: Subject to any disclaimer, the term of this patent is extended or adjusted under 35 U.S.C. 154(b) by 752 days.

(21) Appl. No.: 16/013,522

(22) Filed: Jun. 20, 2018

(65) Prior Publication Data

US 2019/0307436 A1  Oct. 10, 2019

Related U.S. Application Data

(60) Provisional application No. 62/652,367, filed on Apr. 4, 2018.

(51) Int. Cl.
*A61B 10/02* (2006.01)
*A61B 10/04* (2006.01)

(52) U.S. Cl.
CPC .. *A61B 10/0283* (2013.01); *A61B 2010/0208* (2013.01); *A61B 2010/045* (2013.01)

(58) Field of Classification Search
CPC .......... A61B 10/0283; A61B 2010/045; A61B 2010/0208
See application file for complete search history.

(56) References Cited

U.S. PATENT DOCUMENTS

| | | | |
|---|---|---|---|
| 4,306,570 A | 12/1981 | Matthews | |
| 4,758,232 A * | 7/1988 | Chak | A61B 5/15003 |
| | | | 600/578 |
| 5,425,376 A * | 6/1995 | Banys | A61B 10/0275 |
| | | | 600/566 |
| 7,608,048 B2 | 10/2009 | Goldenberg | |
| 8,500,654 B2 | 8/2013 | Goldenberg | |
| 9,078,640 B1 * | 7/2015 | An | A61B 10/0283 |
| 9,149,293 B2 | 10/2015 | Hardert et al. | |
| 9,763,649 B2 | 9/2017 | Hardert et al. | |
| 10,729,856 B1 * | 8/2020 | Nock | A61B 10/0096 |
| 10,765,411 B2 * | 9/2020 | Fisher | A61B 17/3476 |
| 2003/0125639 A1 | 7/2003 | Fisher et al. | |
| 2005/0054947 A1 | 3/2005 | Goldenberg | |
| 2005/0137525 A1 | 6/2005 | Wang et al. | |
| 2005/0165328 A1 | 7/2005 | Heske et al. | |
| 2005/0203439 A1 * | 9/2005 | Heske | A61B 10/0283 |
| | | | 600/566 |
| 2007/0198043 A1 | 8/2007 | Cox et al. | |
| 2008/0058671 A1 * | 3/2008 | Wiksell | A61B 10/0233 |
| | | | 600/566 |
| 2008/0071193 A1 * | 3/2008 | Reuber | A61B 10/0283 |
| | | | 600/567 |

(Continued)

OTHER PUBLICATIONS

Partial European Search Report from the counterpart application serial No. EP18183271.8, dated Feb. 4, 2019.

*Primary Examiner* — Sean P Dougherty
(74) *Attorney, Agent, or Firm* — Nicholas Pfeifer; Smith & Hopen, P. A.

(57) ABSTRACT

A syringe is coupled to a biopsy needle through a coupling structure that includes a motor-driven element such as a gear to rotate the needle. The needle can have a sharp beveled tip which, in cooperation with rotation of the needle, harvests tissue in vivo via rotation rather than multiple "sticks" into the patient.

5 Claims, 14 Drawing Sheets

(56) References Cited

U.S. PATENT DOCUMENTS

| | | |
|---|---|---|
| 2009/0118641 A1 | 5/2009 | Dam et al. |
| 2009/0204023 A1 | 8/2009 | Goldenberg |
| 2011/0301496 A1* | 12/2011 | Lampropoulos ... A61B 10/0283 600/562 |
| 2013/0131547 A1 | 5/2013 | Hardert et al. |
| 2015/0105690 A1* | 4/2015 | Hathaway .......... A61B 10/0275 600/566 |
| 2016/0022250 A1 | 1/2016 | Hardert et al. |
| 2016/0120517 A1* | 5/2016 | AlMaatouq ........ A61B 10/0275 600/566 |
| 2017/0055965 A1* | 3/2017 | Flatland ............. A61B 10/0266 |
| 2017/0055966 A1* | 3/2017 | Vetter .................. A61M 1/007 |
| 2017/0303889 A1* | 10/2017 | Grim ..................... A61B 8/462 |
| 2017/0325792 A1 | 11/2017 | Hardert et al. |
| 2018/0256138 A1* | 9/2018 | Araujo ............... A61B 10/0266 |
| 2019/0321013 A1* | 10/2019 | Nieminen ...... A61B 17/320068 |

* cited by examiner

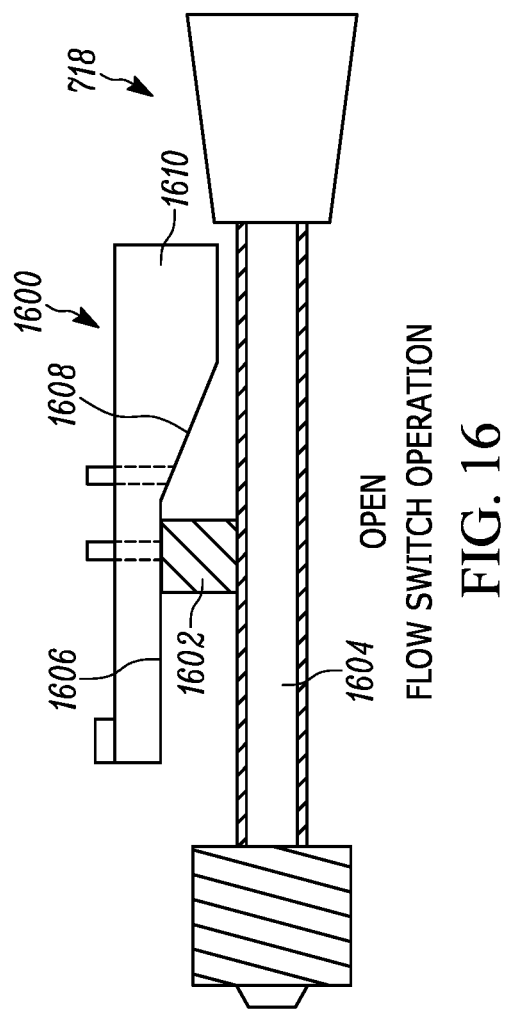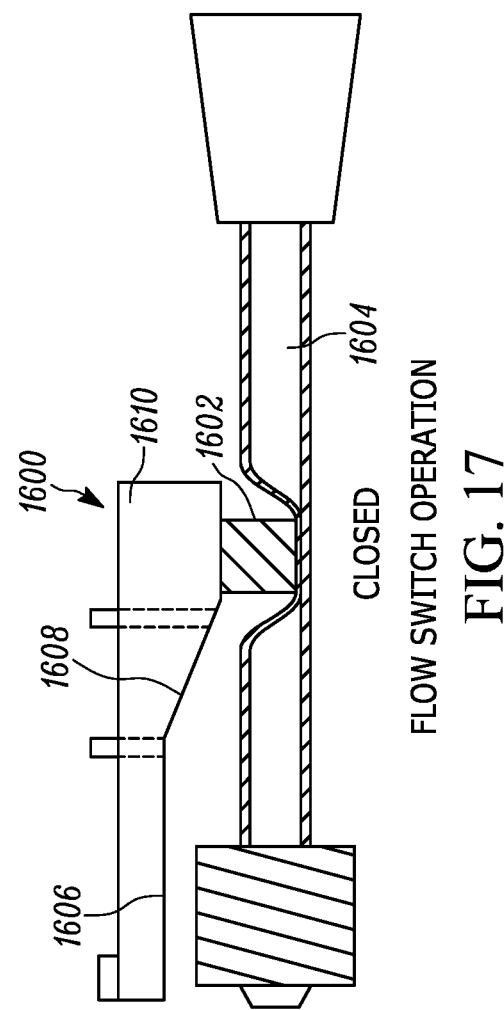

ROTATABLE SYRINGE SYSTEM

FIELD

The application relates generally to rotatable syringe systems, and more particularly to biopsy syringe systems with rotatable needles.

BACKGROUND

It may be necessary to extract tissue from a patient for analysis to support diagnosis. For example, it may be necessary to extract tissue for "cytological" or cell harvest, as well as cores of tissue for breast biopsies, to ascertain the existence of disorders of the tissue.

Tissue extraction may be done by inserting a needle into the patient to withdraw tissue into the needle, which is then removed from patient for dispensing the tissue onto analysis equipment.

SUMMARY

As understood herein, it is often necessary to make multiple needle insertions in the patient to obtain sufficient tissue for analysis. Multiple "sticks" is a drawback for both patient comfort and clinical efficiency. Occasionally the need for further biopsy "sticks" is not realized until after the patient has left the medical establishment and a technician discovers that insufficient tissue has been harvested for analysis, requiring the patient to return for additional, uncomfortable tissue harvesting.

Accordingly, to avoid drawing tissue samples of insufficient cells that as a consequence requires repetition, a rotating needle is driven by a motor to harvest significantly higher yields of cellular material, reducing cost and patient discomfort.

In an aspect, a device includes an elongated needle having a cutting tip and a hollow interior. A syringe is coupled to the needle for rotation of the needle relative to the syringe, with an evacuatable tissue chamber being established at least in part by the hollow interior of the needle. A motor is coupled to the needle to rotate the needle while the tissue chamber is evacuated, and the needle is disposed adjacent tissue to facilitate drawing cells from the tissue into the tissue chamber.

In example embodiments, the syringe includes a distal end configured as a connector, the needle is engaged with a needle hub, and the syringe is coupled to the needle by a coupling comprising at least a mating connector for the needle hub and a mating connector for the syringe connector. The example syringe includes a barrel and a plunger slidably disposed in the barrel and movable to evacuate the tissue chamber, and a valve such as a slide valve or stopcock or other valve structure is operably coupled to the coupling to lock vacuum in the tissue chamber.

In non-limiting implementations, the coupling may include at least one hollow fitting engaged with the needle hub. The hollow fitting includes a body that may be configured as a Luer fitting and a driven gear circumscribing the body and meshed with a drive gear coupled to the motor. At least one support assembly is engaged with the hollow fitting to rotatably support the hollow fitting. The support assembly is coupled to the connector of the distal end of the syringe, if desired via at least one Luer fitting. The hollow fitting that is engaged with the needle hub may rotate against an O-ring engaged with the support assembly.

In some implementations, the motor defines an axis of rotation, the needle defines a longitudinal axis, and the axis of rotation of the motor is co-linear with the longitudinal axis of the needle. In other implementations, the motor defines an axis of rotation, the needle defines a longitudinal axis, and the axis of rotation of the motor is offset from with the longitudinal axis of the needle. In this implementation a belt may couple the motor to the needle to cause the needle to rotate under influence of the motor. Or, driven and drive gears may couple the motor to the needle to cause the needle to rotate under influence of the motor.

In some examples, the needle is no larger than twenty-five (235) gauge and may be 25 gauge or 27 gauge. The needle may rotate at a speed in the range of sixty (60) revolutions per minute (RPM) to three hundred fifty (350) RPM, inclusive.

In example implementations, the syringe can include a barrel and a plunger slidably disposed in the barrel and proximally movable to evacuate the tissue chamber, and a plunger lock can be mounted on a proximal portion of the barrel. At least one notch can be formed in the plunger, with at least a portion of the plunger lock riding against the plunger until the notch is juxtaposed with the portion of the plunger lock to cause the portion of the plunger lock to engage the notch to impede distal movement of the plunger. The plunger can be rotatable in the barrel to disengage the portion of the plunger lock from the notch.

In another aspect, a device includes a needle, a needle hub supporting the needle, and a rotatable fitting connected to the needle hub. The rotatable fitting includes a body and a driven gear circumscribing the body. A support assembly is rotatably engaged with the rotatable fitting, and a syringe is coupled to the support assembly by at least one coupling. A fluid passageway for fluid communication between an interior of the needle and the syringe is established by the needle hub, rotatable fitting, and support assembly such that the syringe is manipulable to evacuate the interior of the needle. A motor is coupled to a drive gear that in turn is meshed with the driven gear to cause the needle to rotate under influence of the motor while the interior of the needle is evacuated.

In another aspect, a method includes retracting a syringe plunger proximally relative to a barrel of the syringe to a first proximal position and closing a vacuum opening in the barrel. After closing the vacuum opening, the method includes retracting the syringe plunger proximally relative to the barrel of the syringe to a second proximal position to evacuate the barrel. The second proximal position is more proximal than the first proximal position. The method includes advancing a needle in fluid communication with the barrel of the syringe into an object to be sampled, energizing a motor coupled to the needle to rotate the needle, and opening the vacuum opening to cause portions of the object to be sucked into the needle as the needle rotates. The method then includes deenergizing the motor, releasing the vacuum, withdrawing the needle from the object, and advancing the plunger distally to expel the portions of the object from the needle.

The details of the present application, both as to its structure and operation, can best be understood in reference to the accompanying drawings, in which like reference numerals refer to like parts, and in which:

BRIEF DESCRIPTION OF THE DRAWINGS

FIGS. 16 and 17 are schematic side diagrams of the slide valve shown in FIGS. 7 and 9 in the open and closed configurations, respectively.

DETAILED DESCRIPTION

Figure 1:
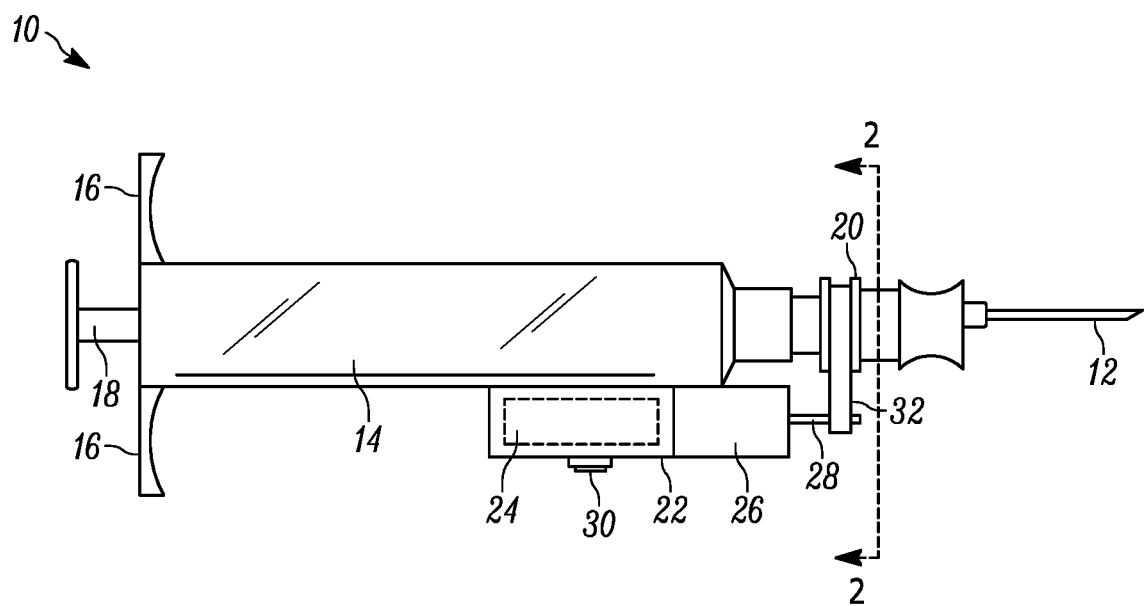
FIG. 1 is a side elevational view of a rotatable syringe system consistent with present principles.

FIG. 1 illustrates a rotatable syringe system 10 that includes a barrel, a needle, a plunger, and a drive assembly. The rotatable syringe system 10 is for capturing tissue from within a patient and extracting from within the patient the captured tissue for analysis in a safe, convenient, and economical manner. In this context and as described more fully below, first provided is a barrel having a distal end and a proximal end. The proximal end of the barrel has laterally extending finger supports. A needle is provided having a distal end and a proximal end. The proximal end of the needle is operatively coupled to the distal end of the barrel. A plunger is provided having a distal end and a proximal end. The distal end of the plunger is coupled to the barrel. The proximal end of the plunger is adapted to be contacted by a thumb of a care giver with fingers on the finger supports. A drive assembly is also provided. The drive assembly includes a housing with a distal end and proximal end. A source of electrical potential is provided within the housing. A motor is operatively coupled to the needle. A switch on the housing functions to inactivate the motor and to activate the motor to rotate the needle.

Now describing the details of FIG. 1, the syringe system 10 includes a rotatable needle 12 for capturing tissue from within a patient and for extracting from the patient captured tissue for analysis. The needle 12 is coupled to a syringe that includes a barrel 14 formed in a cylindrical configuration and adapted to receive and support and dispense liquid such as medication.

The barrel 14 has a distal end and a proximal end. The proximal end has laterally extending finger supports 16. The needle 12 also has a distal end and a proximal end, and the distal end of the needle is formed with a point. The proximal end of the needle is operatively coupled to the distal end of the barrel.

The syringe also includes a plunger 18 with a distal end and a proximal end. The distal end of the plunger is located within the barrel 14 to advance liquid medication out of the barrel into and through the needle and into the patient. The proximal end of the plunger is adapted to be depressed by a thumb of a care giver with fingers on the finger supports. The barrel 14 and the needle 12 and the plunger 18 share a common central axis.

A pulley 20 is next provided. The pulley 20 is located between the proximal end of the needle 12 and the distal end of the barrel 14. The pulley 20 is attached to the needle for rotational movement therewith but with no axial movement of the needle. The pulley 20 is coupled to the barrel 14 for rotation independent of the barrel 14.

Next, a drive assembly is provided. The drive assembly includes a housing 22 in a cylindrical configuration with a distal end and proximal end. A source 24 of electrical potential is provided within and adjacent to the proximal end of the housing. A motor 26 is provided within the housing 22 adjacent the distal end of the housing 22. A drive shaft 28 is coupled to the motor 26. The drive shaft 28 extends forward from the motor 26 and the housing 22 to a location laterally spaced from the pulley 20. A switch 30 is provided to activate and inactivate the motor 26.

A belt 32 is trained around the drive shaft 28 and the pulley 20 to rotate the pulley 20 and the needle 12 for capturing tissue from within a patient and for extracting from the patient captured tissue for analysis.

Figure 2:
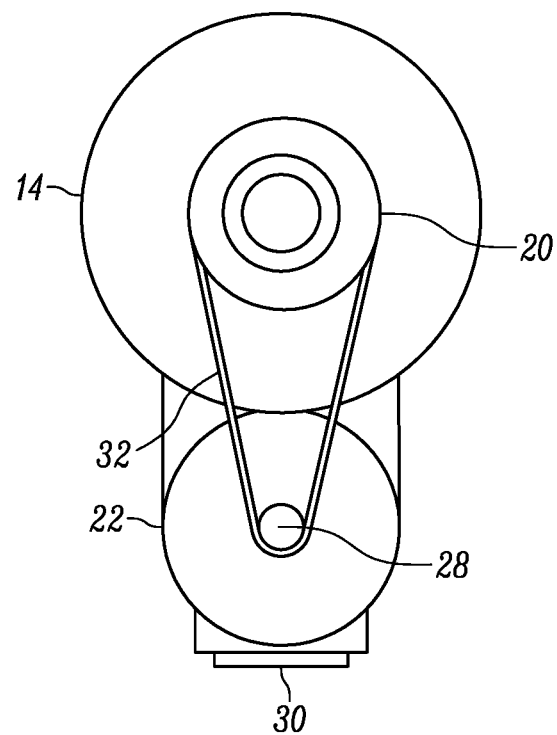
FIG. 2 is a front elevational view of the system shown in FIG. 1.

FIGS. 3-6 show alternate embodiments that may incorporate the structure shown in FIGS. 1 and 2, with the following exceptions.

Figure 3:
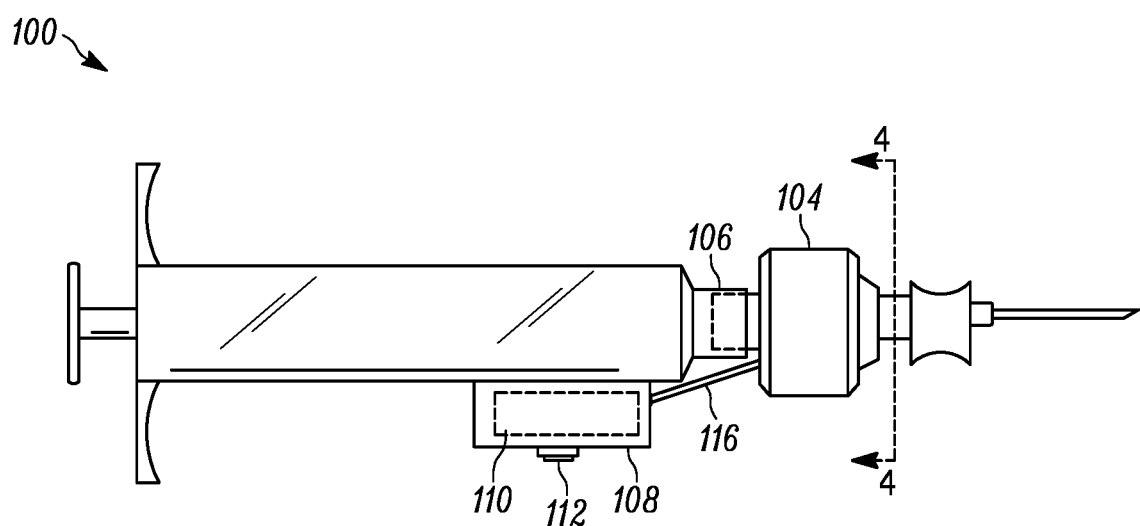
FIG. 3 is a side elevational view of a rotatable syringe system constructed in accordance with an alternate embodiment consistent with present principles.
Figure 4:
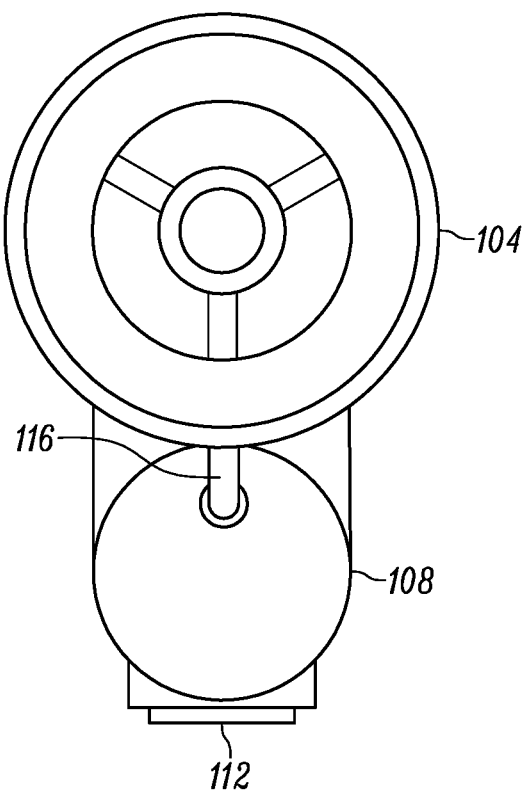
FIG. 4 is a front elevational view of the system shown in FIG. 3.

FIGS. 3 and 4 illustrate an alternate system 100 with an in-line motor 104 located between the barrel of a syringe and a rotatable needle. The system 100 includes a housing 108 of a reduced size compared to the housing 22 shown in FIG. 1 and coupled to the barrel of the syringe. A source 110 of electrical potential is centrally located within the housing 108, and a switch 112 is centrally located on the housing to activate and deactivate the motor 104. A wire 116 couples the motor 104 and the source 110 of electrical potential.

Figure 5:
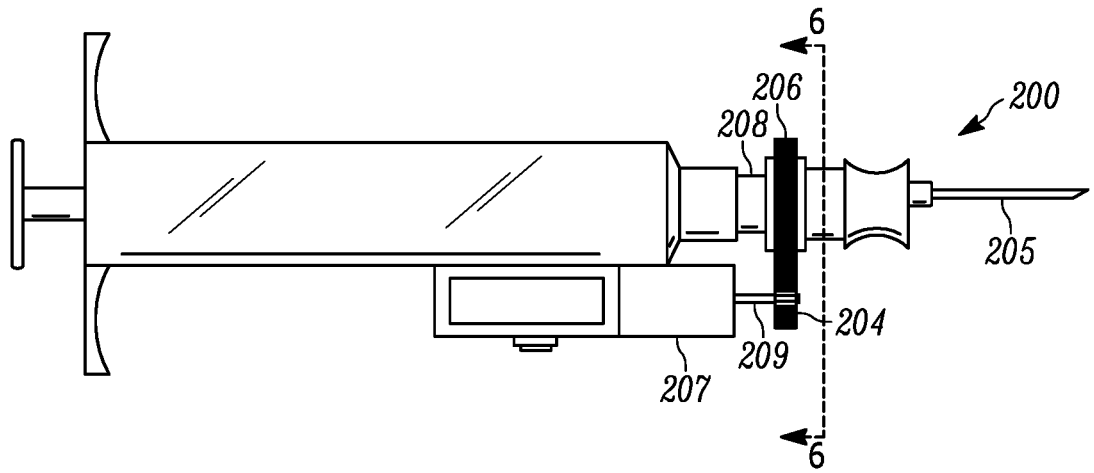
FIG. 5 is a side elevational view of another alternate embodiment consistent with present principles.
Figure 6:
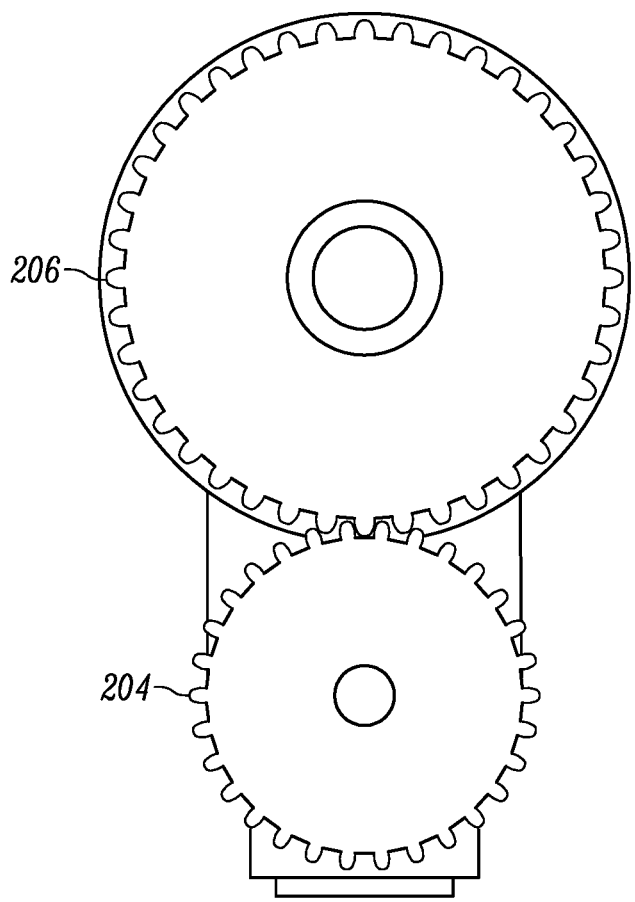
FIG. 6 is a front elevational view of the system shown in FIG. 5.
Figure 7:
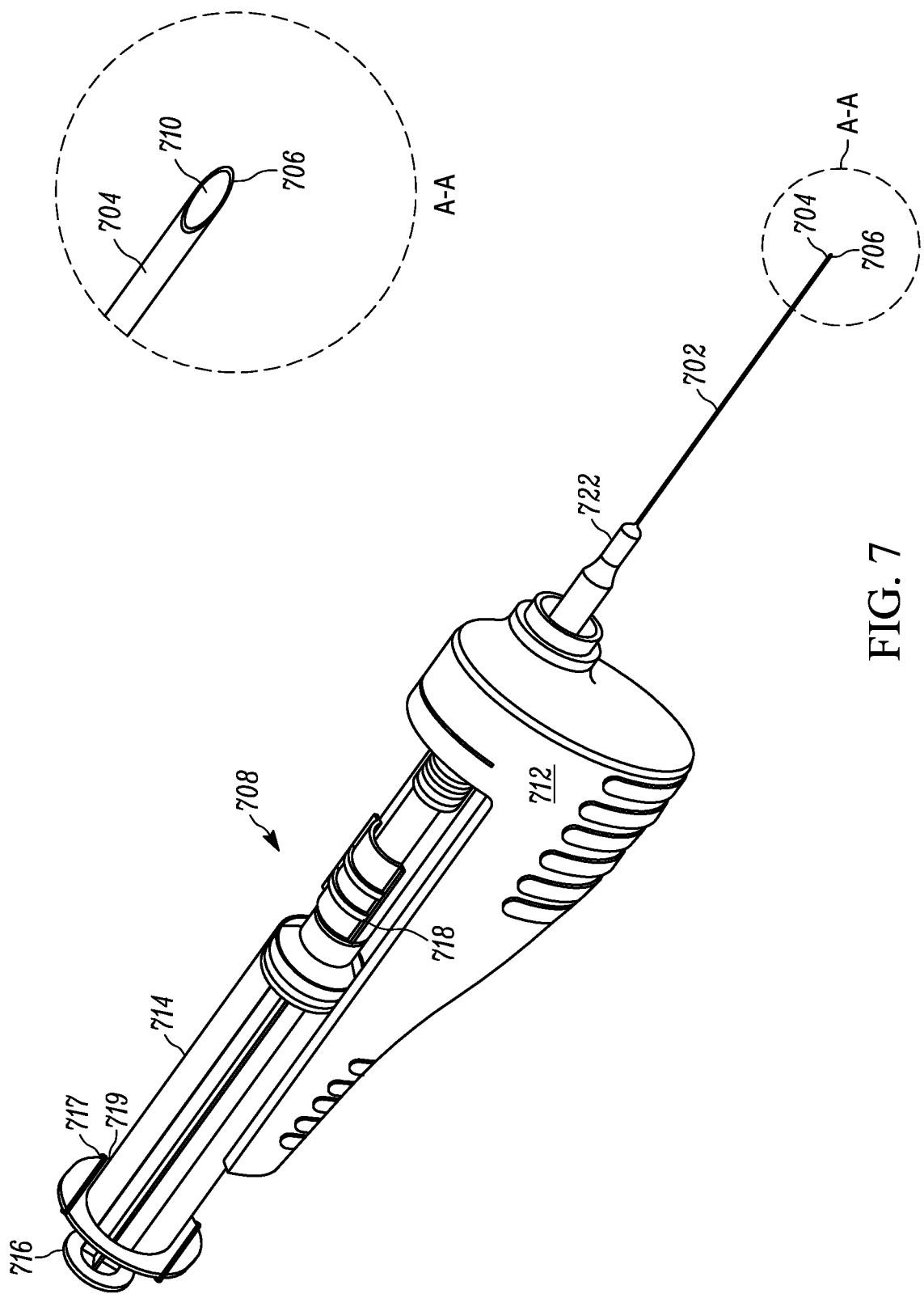
FIG. 7 is a perspective view of a first embodiment of a motor-driven needle assembly, showing a vacuum valve configured as a slide valve.

FIGS. 5 and 6 show yet another embodiment, a specific example of which is illustrated in FIG. 7 et seq. As shown, a driven gear 206 is coupled to needle 205 to rotate the needle 205. A motor is in a housing 207 with a drive shaft 209 extending forward of the housing 207 to a location laterally spaced from the driven gear 206. A drive gear 204 on the drive shaft 209 is meshed with the driven gear 206 for rotating the driven gear 206 and the needle 205.

In operation, any of the needles described herein can be placed at the edge of the tissue, such as a nodule, under ultrasound imaging or other imaging techniques such as ultrasound computed tomography (CT) guidance, magnetic resonance imaging (MRI) fluoroscopic guidance, and MRI imaging guidance. When the distal end of the plunger is withdrawn, a vacuum is created in the needle to withdraw tissue to be analyzed. The motor is energized with the switch on the syringe so that the procedure can be done with one hand. Once activated, the rotating needle is advanced in and out of the lesion, changing direction with each pass if desired. Once a sample is seen in the needle hub or syringe, the motor can be turned off and the needle removed. The sample can then be placed on slides for pathology evaluation. The motor can cause the needle to spin from 60 to 350 revolutions per minute (RPM), depending on what is determined to be the optimum speed. The needle may be advanced into the tissue sample for a period of 10 to 30 seconds or until a blood drop appears in the hub of the needle or syringe. During the fine needle aspirating (FNA), the rotating needle, preferably a 25 gauge needle, will be well visualized under ultrasound imaging. There will be for the most part only one pass into the nodule needed due to the highly effective cell shearing action of the rotating needle.

Now referring to FIG. 7, a device 700 includes an elongated needle 702. The needle 702 may be a hollow metal hypodermic needle of a size of no more than twenty-five gauge (i.e., 25 gauge or greater gauge) with a cutting tip 704 as shown in detail A-A. The cutting tip 704 has a sharp cutting edge 706 that may be beveled as shown to facilitate cutting tissue when the needle 702 is advanced into tissue and rotated.

A syringe 708 is coupled to the needle 702 for rotation of the needle 702 relative to the syringe 708. An evacuatable tissue chamber 710 is established at least in part by the hollow interior of the needle 702. A motor, shown and described further below, is supported in a drive housing 712 and is coupled to the needle 702 to rotate the needle 702 while the tissue chamber 710 is evacuated and the needle 702 is disposed adjacent tissue to facilitate drawing cells from the tissue into the tissue chamber 710.

The syringe 708 typically includes a barrel 714 and a plunger 716 slidably disposed in the barrel 714 and movable to evacuate the tissue chamber 710. A valve such as a slide valve 718 (FIG. 7) or three-way stopcock 800 (FIG. 8) or other valve structure may optionally be provided to lock vacuum in the tissue chamber 710, although in some embodiments vacuum is established by appropriate manipulation of the syringe without the need for a valve. It is to be understood that the embodiment of FIG. 8 may in all other essential respects be identical to that of FIG. 7, with FIG. 8 additionally showing that the needle may be encased in a removable safety guard 802.

Completing the description of FIG. 7, in some embodiments a plunger lock mechanism 717 is engaged with the barrel 714, in this case with a proximal thumb flange 719 of the barrel 714, to engage one or more notches in the plunger 716 to impede advancing the plunger into the barrel (and for that matter to impede withdrawing the plunger out of the barrel). As more fully disclosed below, the plunger lock mechanism includes a stiff wire-like structure with a segment riding against the plunger 716 as the plunger is withdrawn proximally until the notch is juxtaposed with the segment to cause the segment to engage the notch under material bias. The plunger 716 can be rotatable in the barrel 714 to disengage the segment from the notch.

Figure 8:
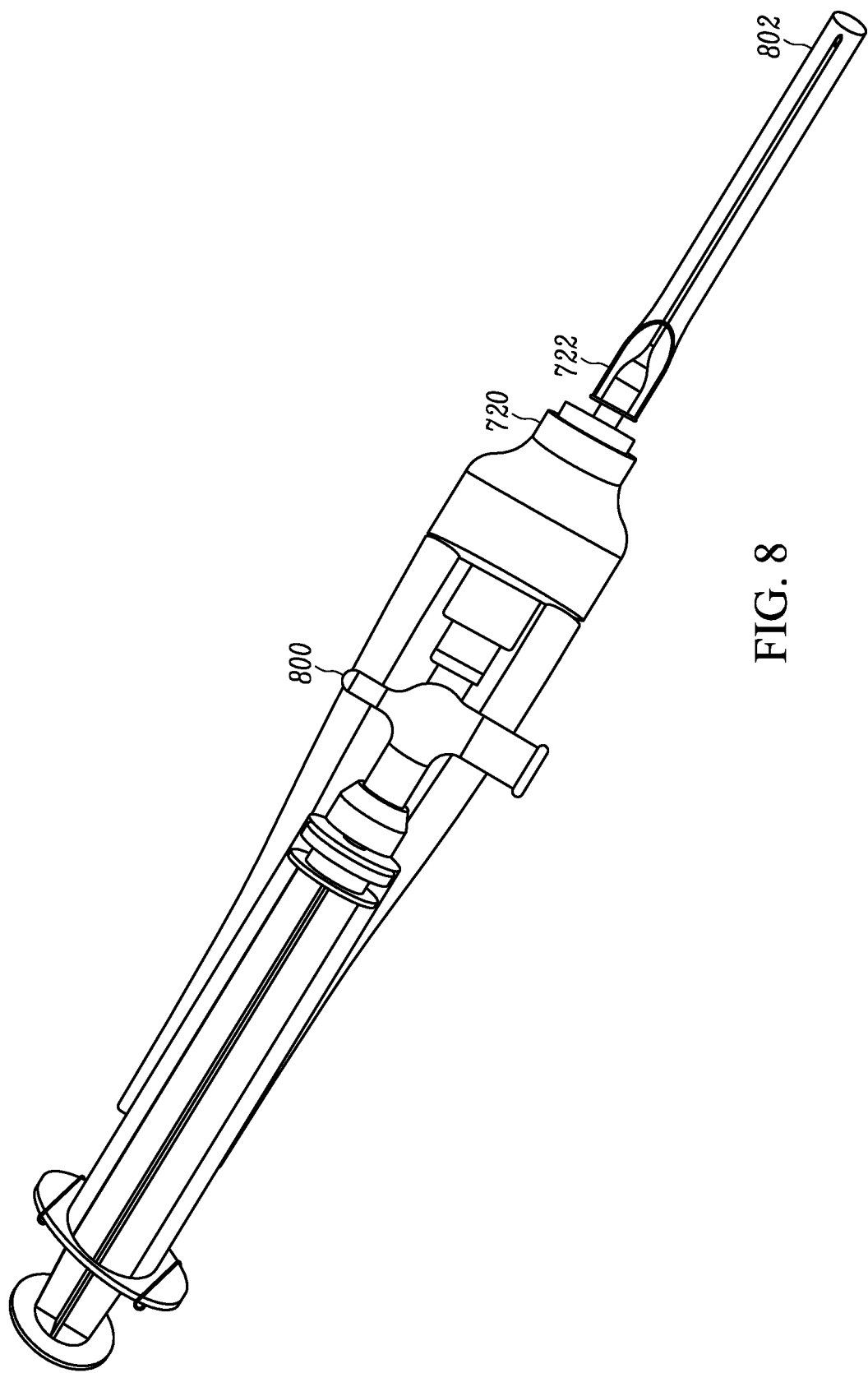
FIG. 8 is a perspective view of a second embodiment of a motor-driven needle assembly, showing a vacuum valve configured as a stopcock.

In example embodiments, as best shown in FIG. 8 the syringe can includes a distal end configured as a connector 720 (the distal end of the syringe 708 is obscured by the drive housing 712 in FIG. 7). The connector 720 may be configured as a Luer fitting. As shown in FIGS. 7 and 8, the needle 702 is engaged with a needle hub 722, and the syringe 708 is coupled to the needle 702 by a coupling that includes at least the needle hub 722 and the connector 720. The needle hub 722 can be established by a hollow Luer fitting such as a female Luer fitting.

Figure 9:
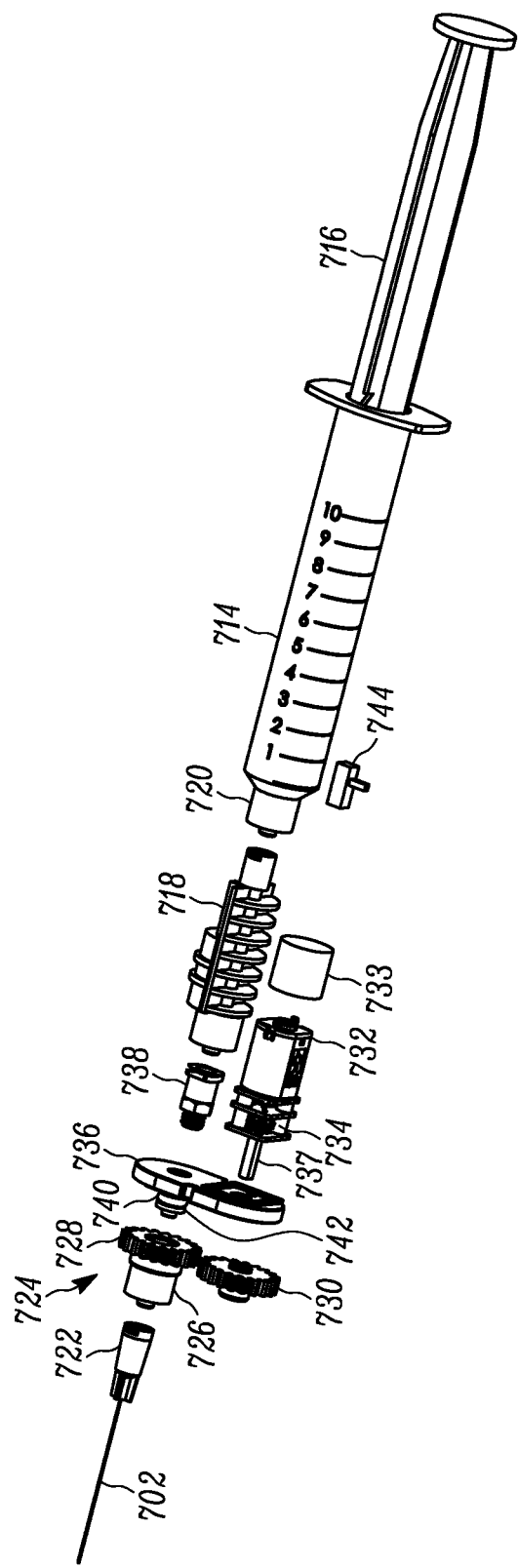
FIG. 9 is an exploded perspective of the assembly of FIG. 7 with the drive housing removed to show components internal to the drive housing.
Figure 10:
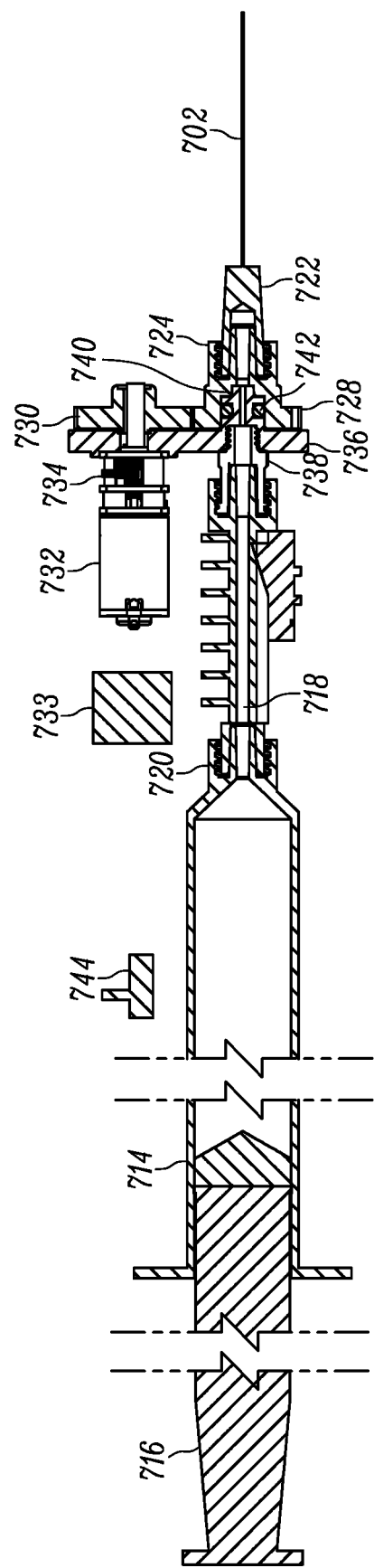
FIG. 10 is a side cut-away view of the needle assembly in FIG. 7 with the drive housing removed to show components internal to the drive housing.

Indeed, and now referring to FIGS. 9 and 10, the above-mentioned coupling may include a hollow fitting 724 engaged with the needle hub 722. In the example shown, the hollow fitting 724 includes a body 726 that may be configured as a male Luer fitting and a driven gear 728 circumscribing the body 726 and meshed with a drive gear 730 that is coupled to a small electric dec-powered motor 732 through a reduction gear assembly 734, which reduces rotational speed to be between sixty (60) revolutions per minute (RPM) to three hundred fifty (350) RPM, inclusive (which is therefore the rotational speed of the needle 702). The motor may be a six-volt DC gear motor operating at three VDC and powered by a battery 733 in the motor housing. These specifications are examples only. A Lithium or alkaline or other type of battery may be used, and the motor could operate at other voltages, e.g., 12 VDC operated by a 9 VDC battery.

A support assembly 736 may be engaged with the hollow fitting 724 to rotatably support the hollow fitting 724. Note that the output shaft 737 of the gear assembly 734 may extend through a hole of the support assembly 736 to connect to the drive gear 730, with the support assembly 734 radially supporting the output shaft 737 as the shaft spins.

The support assembly 736 is coupled to the connector 720 of the distal end of the syringe 708, if desired via at least one Luer fitting 738 that may be, e.g., glued to the support assembly 736. When the slide valve 718 is included (or another valve such as a stopcock as set forth further below), the Luer fitting 738 is connected to the distal end of the valve 718, which in turn is connected at its proximate end to the connector 720 of the syringe. The valve connectors may be configured as Luer fittings. A continuous fluid passageway is formed from the tip of the needle 702 into the barrel 714 of the syringe by the train of components described above, with the valve 718 being operable to selectively occlude the fluid passageway to draw a vacuum in the system when the plunger is retracted proximally.

The hollow fitting 724 may rotate on a boss 740 of the support assembly 736, against an O-ring 740 that circumscribes the boss 740 to establish a fluid seal between the support assembly 736 and hollow fitting 724 during rotation.

As can be appreciated in reference to in FIGS. 9 and 10 and as mentioned above, a fluid passageway for fluid communication is established between the interior of the needle 702 and the syringe 708 by the needle hub 722, rotatable fitting 724, and support assembly 736 such that the syringe 708 is manipulable to evacuate the interior of the needle. The motor 732 that is coupled to the drive gear 730 that in turn is meshed with the driven gear 728 can be energized using a manipulable switch 744 such as a slide switch, toggle switch, moment switch, or other appropriate electrical switch to cause the needle 702 to rotate under influence of the motor 732 while the interior of the needle 702 is evacuated.

Figure 11:
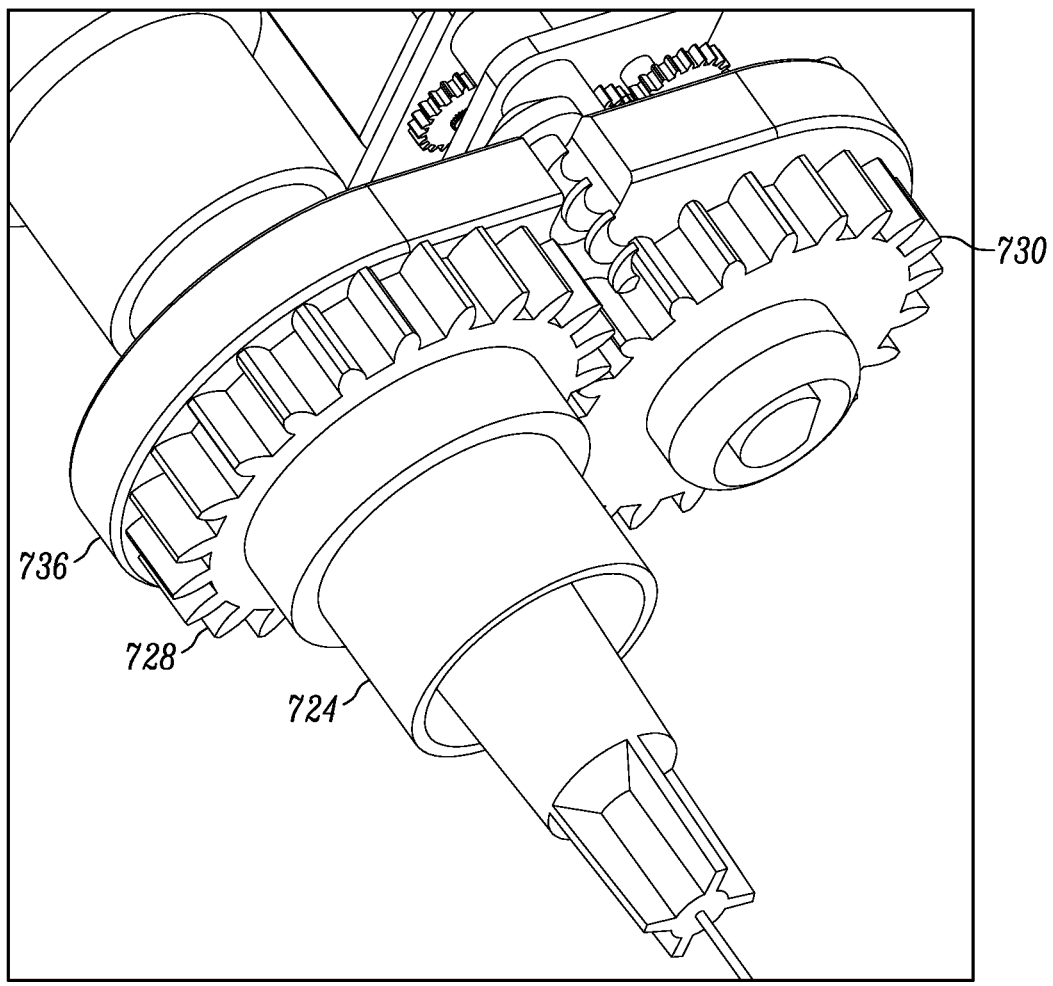
FIG. 11 is a perspective view of the interior of the distal portion of the needle assembly of FIG. 10, showing the rotatable coupling with driven gear meshed with the motor drive gear.
Figure 12:
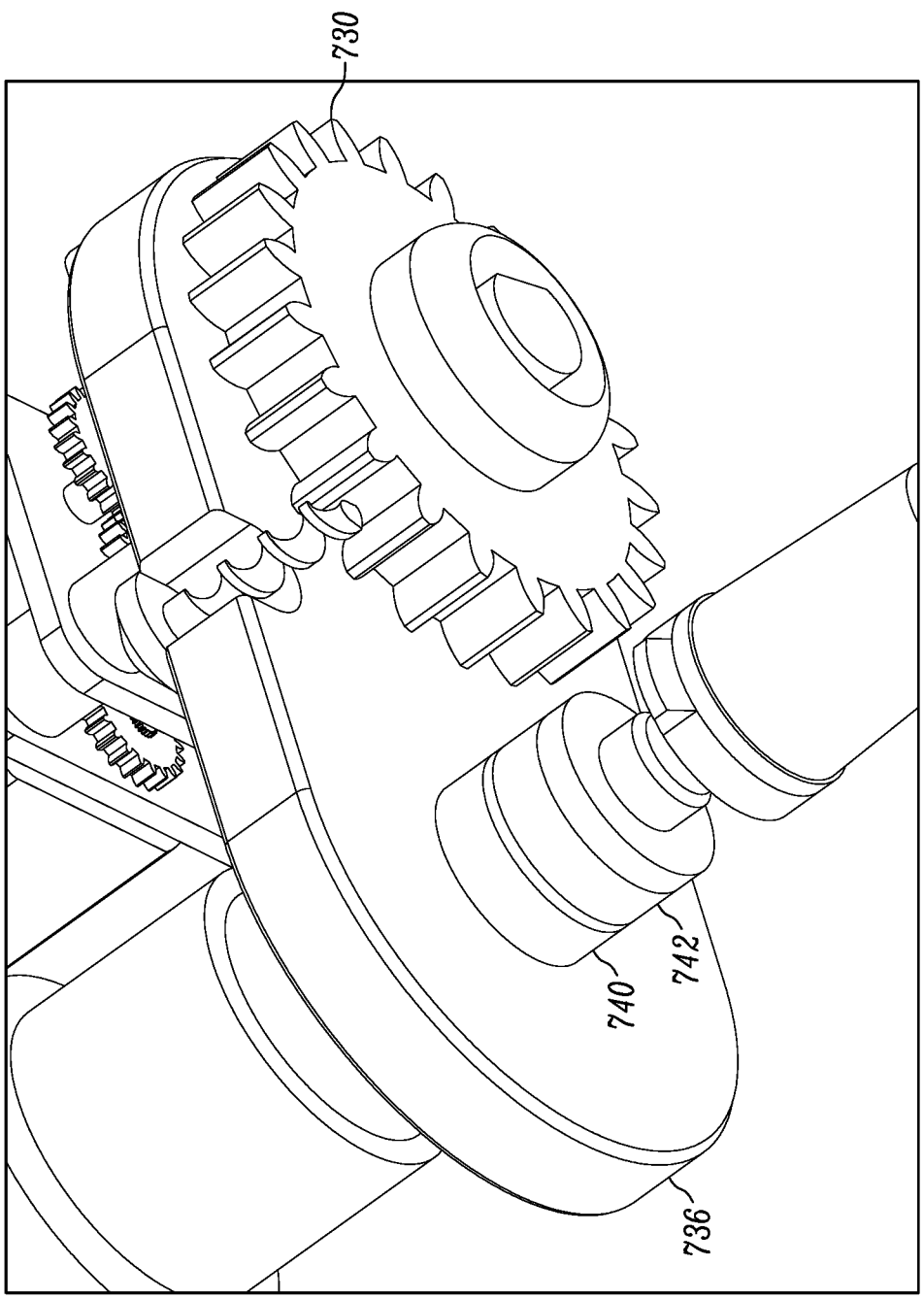
FIG. 12 is a perspective view similar to FIG. 11, with the rotatable coupling removed to show the support boss and o-ring.

FIGS. 11 and 12 together provide further illustration of the drive gear 730, the driven gear 728 (FIG. 11 only), the rotatable fitting 724 (FIG. 11 only), the boss 740 and o-ring 742 (FIG. 12 only), and the support assembly 736.

Figure 13:
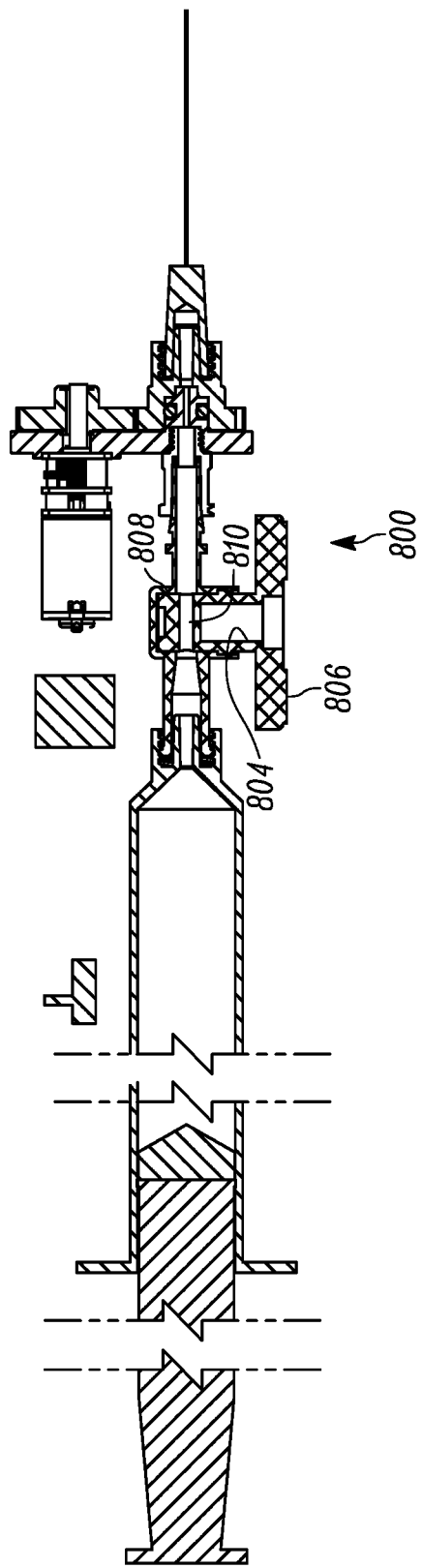
FIG. 13 is a side cut-away view of the needle assembly in FIG. 8 with the drive housing removed to show components internal to the drive housing.

Now referring to FIG. 13, details of the stopcock 800, which may be a one-way stopcock or three-way stopcock, are shown. A cylindrical shaft 804 extending radially from a turnable handle 806 is rotationally engaged within a cylindrical housing 808. A cross hole 810 extends across the shaft 804 such that when the handle 806 is turned, the cross hole 810 is aligned with the proximal and distal outlets of the housing body 808 to allow flow from the needle to the syringe. Reversing the handle turn by 90 degrees seals off the cross hole 810 to block flow of material, fluids or air.

In operation, in some embodiments two to three drops of cells are sought to be obtained from tissue, to be dispensed as discussed below onto a microscope slide for analysis. This amount of sample typically can be held within the needle and hub alone, but to provide indication of adequate tissue harvest, enough tissue may be excised to fill not only the needle but also the fluid passageway between the syringe and needle and into the syringe, where tissue can be visualized and hence indicate sufficient sample has been obtained. With this in mind, the portion of the fluid passageway between the syringe and needle may be considered to be "dead space" which preferably is minimized in volume by making the diameter of the fluid passageway as small as practicable, since the fluid passageway must be filled with sample material before the caregiver sees anything in the syringe.

Figure 14:
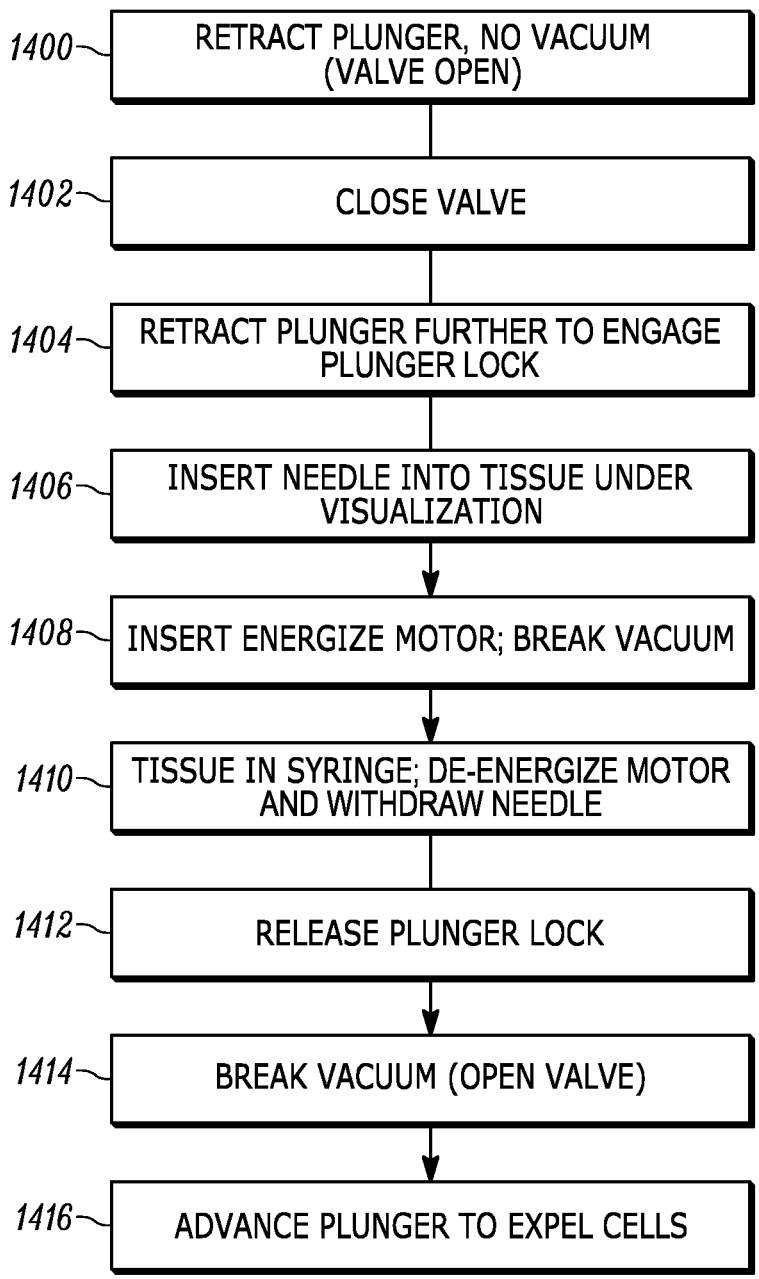
FIG. 14 is a flow chart of example use.

FIG. 14 is a flow chart of example use. At block 1400, the plunger is retracted, e.g., two to three milliliters, without creating a vacuum. When a vacuum valve is used, this is done by opening the valve to allow air into the barrel. After initial plunger retraction, the vacuum valve is closed at block 1402 and then at block 1404 the plunger is retracted further in the proximal direction until the plunger lock 1300 engages the plunger as described above. This creates a vacuum in the syringe.

At block 1406 the needle is next advanced into the target tissue. This procedure preferably is done in conjunction with ultrasound imaging. The ultrasound probe is held with one hand to image where the needle is and the target tissue.

Proceeding to block 1408, the motor is energized using, e.g., a slide switch, a moment switch, or other activating element. Vacuum in the syringe is broken by, e.g., opening the vacuum valve, which causes cells from the tissue to be sucked into the needle through the cutting tip with the needle constantly rotating the entire time. When tissue is visualized in the needle hub or syringe, indicating sufficient harvest, the motor is deenergized at block 1410, the vacuum is blocked, and the needle withdrawn from the patient.

Moving to block 1412, the plunger lock is released. Opening the vacuum valve without releasing the plunger should be avoided, as this will result in all the cells surging up into the syringe. When the plunger lock is released it will return to the relaxed position it assumed at block 1400, with some air, e.g., two to three milliliters, remaining in the barrel. At this point, at block 1414 the vacuum valve is opened. Moving to block 1416, the plunger is advanced distally to expel the cells out of the tip of the needle, typically onto a microscope slide for analysis. Note that owing to the small needle gauge in some embodiments, tissue cores are not harvested, only cells that are scraped from the tissue by the rotating needle.

While FIG. 14 illustrates details of an example method, another method attendant to FIG. 15 below includes retracting the plunger slightly, advancing the needle under visualization such as ultrasound guidance to the target tissue or lesion, actuating the motor to rotate needle, retracting the plunger to create vacuum in the needle while the motor is spinning, releasing the plunger, deactivating the motor, retracting the needle from the patient, and dispensing the cells on a slide.

Figure 15:
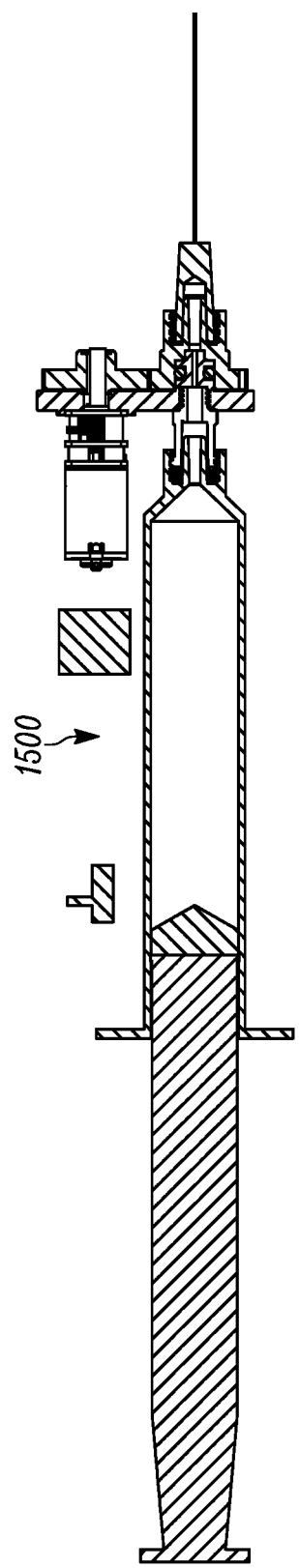
FIG. 15 is a side cut-away view of the needle assembly that in all essential respects is identical to FIGS. 10 and 13, except no vacuum valve or plunger lock are used.

FIG. 15 shows an embodiment 1500 that in all essential respects is identical to those shown in FIGS. 7 and 8 and supporting figures, except that the vacuum valve and plunger lock are omitted, with different plunger manipulations used to perform use steps. Specifically, as mentioned above the procedure may be commenced with the plunger partially retracted, which provides enough plunger travel to create vacuum when needed and leaving some air volume in storage to dispense the cells. With the plunger partially retracted (essentially, step 1400 in FIG. 14), the needle is advanced into the tissue (essentially, step 1406 in FIG. 14), and the motor is energized to spin the needle to excise tissue (essentially, part of step 1408 in FIG. 14). At the same time, the plunger is retracted further proximally while the needle is spinning to draw tissue into the needle. Step 1410 in FIG. 14 is then performed to stop the motor and withdraw the needle, and then the process proceeds directly to step 1416 to expel tissue from the needle by advancing the plunger into the barrel of the syringe.

FIGS. 16 and 17 show example details of the slide valve 718. A slide 1600 can move longitudinally relative to the syringe to an open configuration (FIG. 16), in which a rigid compression block 1602 is disposed between a tube 1604 and a thinner section 1606 of the slide 1600 to allow the tube 1604, which like other tubes herein may be resilient, to remain open under material bias. The slide 1600 can move to a closed configuration (FIG. 17). When moving from the open to the closed configurations, a beveled section 1608 of the slide 1600 rides against the compression block 1602 to press the compression block 1602 against the tube 1604, a thick portion 1610 of the slide 1600 eventually reaching the compression block 1602 to completely occlude the tube 1604 in the closed configuration of FIG. 17.

Figure 18:
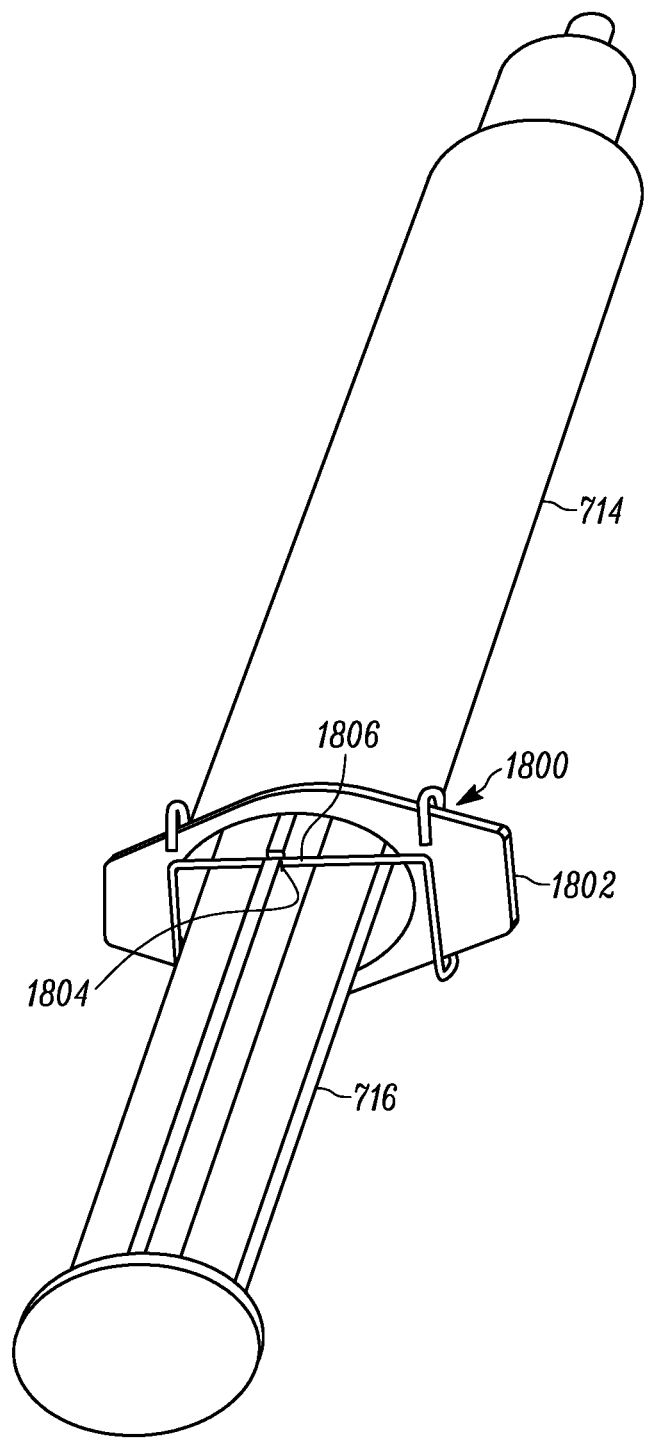
FIG. 18 is a schematic view of a plunger lock mechanism with distal components including the needle and related drive train not shown for simplicity.

Now referring to FIG. 18, the plunger 716 of the syringe 708 that is slidably disposed in the barrel 714 is proximally movable to evacuate the tissue chamber. A stiff wire-like plunger lock 1800 can be mounted on a proximal portion 1802 of the barrel 714, in this case, a flat thumb surface. One or more notches 1804 can be formed in the plunger 716, with at least a segment 1806 of the plunger lock 1800 riding against the plunger 716 as the plunger is withdrawn proximally until the notch 1804 is juxtaposed with the segment 1806 of the plunger lock 1800 to cause the segment 1806 of the plunger lock 1800 to engage the notch 1804 to impede distal movement of the plunger 716. The plunger 716 can be rotatable in the barrel 714 to disengage the segment 1806 of the plunger lock 1800 from the notch 1804.

In some examples, a flexible shaft design may implement the rotational train of elements above and advanced down a bronchoscope or other endoscope. The needle may be larger than twenty-five gauge if desired to harvest tissue cores for biopsies.

While the particular device is herein shown and described in detail, it is to be understood that the subject matter which is encompassed by the present invention is limited only by the claims.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B. C") includes systems that have A alone, B alone, C alone, A and B together, A and C together, B and C together, and/or A, B, and C together, etc.

What is claimed is:

1. A device comprising:
   a needle;
   a needle hub supporting the needle;

a rotatable fitting connected to the needle hub;

a support assembly rotatably engaged with the rotatable fitting;

a syringe coupled to the support assembly by at least one coupling, the syringe including a barrel and a plunger slidably disposed in the barrel, the plunger proximally movable to evacuate the tissue chamber;

a wire-like plunger lock removably mounted on a proximal portion of the barrel;

at least one notch formed in the plunger, at least a portion of the plunger lock riding against the plunger until the notch is juxtaposed with the portion of the plunger lock to cause the portion of the plunger lock to engage the notch to impede distal movement of the plunger, the plunger being rotatable in the barrel to disengage the portion of the plunger lock from the notch;

a fluid passageway for fluid communication between an interior of the needle and the syringe being established by the needle hub, rotatable fitting, and support assembly such that the syringe is manipulable to evacuate the interior of the needle; and a motor operably coupled to the needle thereby causing the needle to rotate under influence of the motor while the interior of the needle is evacuated.

2. The device of claim 1, wherein the support assembly comprises a Luer connector connected to the coupling of the syringe.

3. The device of claim 1, wherein the syringe comprises a valve operably coupled to the coupling to occlude the fluid passageway.

4. The device of claim 1, wherein the needle is no larger than twenty-five (25) gauge.

5. The device of claim 1, wherein the needle rotates at a speed in the range of sixty (60) revolutions per minute (RPM) to three hundred fifty (350) RPM, inclusive.

* * * * *